(12) United States Patent
Viegas Nieto Guimaraes (10) Patent No.: US 10,993,847 B2
(45) Date of Patent: May 4, 2021

(54) SURGICAL SWAB COMPOSED OF NON-WOVEN FABRIC AND TEXTILE POLYMER NET

(71) Applicant: BASTOS VIEGAS, S.A., Penafiel (PT)

(72) Inventor: Luis Salvador Viegas Nieto Guimaraes, Vilar do Paraiso (PT)

(73) Assignee: BASTOS VIEGAS, S.A., Penafiel (PT)

( * ) Notice: Subject to any disclaimer, the term of this patent is extended or adjusted under 35 U.S.C. 154(b) by 437 days.

(21) Appl. No.: 15/510,857

(22) PCT Filed: Aug. 24, 2015

(86) PCT No.: PCT/IB2015/056392
§ 371 (c)(1),
(2) Date: Mar. 13, 2017

(87) PCT Pub. No.: WO2016/042429
PCT Pub. Date: Mar. 24, 2016

(65) Prior Publication Data
US 2017/0258642 A1 Sep. 14, 2017

(30) Foreign Application Priority Data
Sep. 17, 2014 (PT) .......................................... 107891

(51) Int. Cl.
*A61F 13/38* (2006.01)
*D04H 1/435* (2012.01)
(Continued)

(52) U.S. Cl.
CPC .......... *A61F 13/36* (2013.01); *A61F 13/2082* (2013.01); *A61F 13/38* (2013.01);
(Continued)

(58) Field of Classification Search
CPC combination set(s) only.
See application file for complete search history.

(56) References Cited

U.S. PATENT DOCUMENTS 5,009,652 A * 4/1991 Morgan .................. A61F 13/36
604/378
5,466,231 A * 11/1995 Cercone .................. A61F 13/36
602/41
(Continued)

FOREIGN PATENT DOCUMENTS

EP 0120710 A2 10/1984
GB 837106 A 6/1960
(Continued)

OTHER PUBLICATIONS

International Search Report and Written Opinion for International Application No. PCT/IB2015/056392 (8 Pages) (dated Jan. 13, 2016).

*Primary Examiner* — Guy K Townsend
(74) *Attorney, Agent, or Firm* — Lucas & Mercante LLP (57) ABSTRACT

The present application describes a surgical swab composed of two or more outer layers made of non-woven fabric and an inner layer of a textile polymer net, with or without x-ray detectable thread, which can be obtained, for example, by a process of knitting or weaving. The textile net can present in its composition materials with high elasticity such as elastane or alternatively combinations of materials that allow shrinking after heat treatment such as the polyamide or polyamide and polyester or even polyamide and cotton. In the present application, it is also described the production process of this surgical swab which, after the junction and overlapping of the non-woven fabric layers and the inner layer of textile polymer net, comprises ultrasound welding of the layers. The surgical swabs of this application present improved performance features and the production process involved is simple, economical and automated.

13 Claims, 4 Drawing Sheets

(51) Int. Cl.
  *D04H 1/555* (2012.01)
  *D04H 1/4374* (2012.01)
  *A61F 13/20* (2006.01)
  *D04H 1/4334* (2012.01)
  *A61F 13/36* (2006.01)

(52) U.S. Cl.
  CPC ........... *D04H 1/435* (2013.01); *D04H 1/4334* (2013.01); *D04H 1/4374* (2013.01); *D04H 1/555* (2013.01)

(56) References Cited

U.S. PATENT DOCUMENTS

| | | | | |
|---|---|---|---|---|
| 5,556,391 A * | 9/1996 | Cercone | ............... | A61F 13/36 602/46 |
| 5,961,500 A * | 10/1999 | Weinstein | ............... | A61F 13/36 602/48 |
| 6,087,549 A * | 7/2000 | Flick | ............... | A61N 1/0496 602/41 |
| 7,790,217 B2 * | 9/2010 | Toreki | ............... | A01N 33/12 427/2.31 |
| 8,092,854 B2 * | 1/2012 | Toreki | ............... | A01N 33/12 427/2.1 |
| 8,118,791 B2 * | 2/2012 | Flick | ............... | A61F 13/00063 604/304 |
| 8,545,862 B2 * | 10/2013 | Toreki | ............... | A61F 13/00063 424/405 |
| 8,801,681 B2 * | 8/2014 | Flick | ............... | A61F 13/00063 424/443 |
| 2004/0243043 A1 * | 12/2004 | McCarthy | ............... | A61F 13/0256 602/46 |
| 2006/0094320 A1 * | 5/2006 | Chen | ............... | D04H 1/4391 442/340 |
| 2006/0264796 A1 * | 11/2006 | Flick | ............... | A61F 13/022 602/48 |
| 2006/0283996 A1 * | 12/2006 | Jensen | ............... | A61F 13/36 241/195 |
| 2008/0125687 A1 * | 5/2008 | Flick | ............... | A61F 13/00063 602/48 |
| 2008/0208100 A1 * | 8/2008 | Wolff | ............... | A61F 13/385 604/1 |
| 2009/0181157 A1 * | 7/2009 | Toreki | ............... | A61L 15/46 427/2.3 |
| 2010/0087713 A1 * | 4/2010 | Eliash | ............... | A61B 17/02 600/206 |
| 2010/0291169 A1 * | 11/2010 | Toreki | ............... | A61L 15/46 424/405 |
| 2010/0330261 A1 * | 12/2010 | Toreki | ............... | A01N 33/12 427/2.31 |
| 2011/0002971 A1 * | 1/2011 | Hassler | ............... | A61K 9/0075 424/404 |
| 2011/0179887 A1 * | 7/2011 | Cobian | ............... | A61B 10/0291 73/864 |
| 2012/0259302 A1 * | 10/2012 | Chaisumdet | ............... | A61F 13/36 604/367 |
| 2013/0185879 A1 * | 7/2013 | Lyon | ............... | D04H 1/555 15/104.93 |
| 2014/0148775 A1 * | 5/2014 | Gawley | ............... | A61F 17/00 604/370 |
| 2016/0278989 A1 * | 9/2016 | Braga | ............... | A61F 13/36 241/195 |
| 2016/0319470 A1 * | 11/2016 | Jenkins | ............... | D04H 1/425 241/195 |
| 2016/0332418 A1 * | 11/2016 | Jenkins | ............... | B32B 27/32 |
| 2017/0156340 A1 * | 6/2017 | Toreki | ............... | D06M 11/46 241/195 |
| 2017/0233909 A1 * | 8/2017 | Wright | ............... | D04H 1/498 428/172 |
| 2017/0258642 A1 * | 9/2017 | Viegas Nieto Guimaraes ............ A61F 13/38 241/195 |

FOREIGN PATENT DOCUMENTS

| | | |
|---|---|---|
| GB | 1521260 A | 8/1978 |
| GB | 2281212 A | 3/1995 |

* cited by examiner

SURGICAL SWAB COMPOSED OF NON-WOVEN FABRIC AND TEXTILE POLYMER NET

CROSS REFERENCE TO RELATED APPLICATION

This Application is a 371 of PCT/IB2015/056392 filed on Aug. 24, 2015, which claims the benefit of Portuguese Application No. 107891 filed on Sep. 17, 2014, the contents of each of which are incorporated herein by reference.

TECHNICAL DOMAIN

The present application describes a surgical swab and the production process thereof.

BACKGROUND

Pre-washed surgical swabs made of hydrophilic gauze are very common articles in the market. In many countries, the use of pre-washed surgical swabs instead of the normal surgical swabs is considered preferred due to the higher absorption capacity and to the spongy and soft touch. The presentation of this type of surgical swabs is very similar to the appearance of reusable surgical swabs, which used to be washed and sterilized after use and have fallen into disuse due to cross-contamination risks.

With the appearance of the non-woven fabric, surgical gauze swabs were largely replaced by surgical non-woven fabric swabs. In this application, it is considered that a non-woven fabric corresponds to a layer of fibres, continuous filaments or chopped threads of any nature or origin, that have been organized into a net by any means, and connected to each other by any method or technology, with the exception of weaving or knitting.

Compared to the traditional gauze swabs, non-woven fabric swabs present higher absorption capacity and rate, suitable resistance, flexibility and adaptability. Since the non-woven fabric swabs are less abrasive and traumatic, they ultimately result in a very comfortable product for the patient. This feature elects this product for all surgical procedures, including the most critical.

Other two key points in the non-woven fabric swabs are the total absence of loose threads and seams. The loose threads, resulting from gauze swabs, may result in infections and even possible complications in the context of an operating room. The absence of threads in the non-woven fabric, completely eliminates this issue as well as the use of sewing threads, usually contaminated with optical brightener. Contrary to the production of gauze swabs which involves very high manipulation in folding and sewing, the production and folding of these swabs is made integrally by machines, in a controlled environment and without handling the product, which guarantees a reduced microbial load. On the other hand, the use of non-woven fabric swabs is advantageous from an environmental point of view and for the protection of natural resources. The gauze swabs are produced from cotton threads. It is estimated that more than 95% of the cotton produced worldwide is obtained using techniques that are harmful to the environment, due to the use of high amounts of pesticides and fertilizers. Its production also requires large amounts of water, the scarcity of this limited resource being a serious environmental threat. Besides all the technical advantages, the non-woven fabric is less expensive than the alternative in gauze, both in terms of production costs and consumption of raw materials.

The surgical non-woven fabric swabs are therefore a very advantageous alternative to the gauze swabs except in what regards the spongy, smooth, appearance, which is possible by means of pre-washing the gauze swabs. The surgical non-woven fabric swabs are generally presented plane, since the pre-wash effect does not have the same result in this material.

The present application discloses a technology with the aim of creating a surgical non-woven fabric swab, presenting structure and features similar to those in the surgical pre-washed gauze swabs. This possibility has been studied before, as described in U.S. Pat. No. 3,683,921. The main objective is to introduce a second element inside the non-woven fabric that, by its technical features, confers wrinkled appearance to the finished article. This second element, the production of non-woven fabric and connection method between different layers are major differences between the product described in U.S. Pat. No. 3,683,921 and the present invention.

The production of non-woven fabric begins with the arrangement of fibres, into a kind of veil or web. One mechanical process to obtain these fibre webs is carding. In this method, the fibres are placed in a carding machine and combed by a cylinder or a series of drums, covered by card clothing or rotating teeth. In order to consolidate the resulting veil from the carding, for several years all non-woven fabrics required the addition of a chemical binding agent to provide structural integrity and to improve its effectiveness. Such non-woven fabric production method is described in U.S. Pat. No. 3,683,921, for the formation of the surgical swab. The veil of fibres formed in the carding is intermeshed with the thermoplastic net via water jets, forming a laminated structure to which a chemical binding agent is subsequently added. In the early 1980s, other bonding technologies grew rapidly and effective methods allowed the industry to produce non-woven fabrics strong and soft without using chemical bonding agents. A major advantage of these new bonding technologies is the fact that the referred non-woven fabrics do not contain formaldehyde or chemical additives.

In U.S. Pat. No. 3,683,921 the intermediate layer consists of a net of a thermoplastic film, in particular polypropylene, which confers the feature of shrinking to the swab, after heat treatment. The formation of this net film is described in detail in document U.S. Pat. No. 3,881,381 and is based on heating a film of a high-density polyethylene or polypropylene at high temperatures, the formation of the net structure and subsequent cooling. The incorporation of this net film within the two layers of fibres enables a contraction in its structure from 3 to 25% due to the "elastic memory" of the film. On the contrary, the technology now presented allows the contraction/shrinking of the swab by inserting a textile mesh net, which can be obtained by the process of knitting or weaving, constructed from materials such as elastane or polyamide and polyester or even polyamide and cotton, between the non-woven fabric layers. In this same document, U.S. Pat. No. 3,683,921, the union between the outer layers of fibres and the thermoplastic film net is carried out through a first passage of these three layers by a system of high pressure water jets, so that the fibres became intermeshed in the thermoplastic net, followed by an application of the binding agent and subsequent curing and drying of the same binding agent. Subsequently, different layers of this reinforced laminate are overlapped, welded by heat and cut to the desired sizes. The welding and cutting on all four sides of the swab of these plastic film layers in a net shape and intermeshed fibres would inevitably produce hard and rough surfaces in the cutting zone. Such steps are not necessary in the present invention, since the outer layers are composed of finished non-woven fabric and without applying any bonding agent. The union between layers is carried out by ultrasound thus allowing the ends of the swab, including the cutting zone, to be soft and flexible.

SUMMARY

The present application describes a surgical swab composed of two or more outer layers of non-woven fabric, one inner layer of textile polymer net, with or without x-ray detectable thread, composed of materials that present high elasticity, such as elastane, or high shrinking capacity after heat treatment, such as polyamide or polyamide and polyester or even polyamide and cotton, features that cause a wrinkled effect in the final article.

In the present application, it is also described the production process of this surgical swab that, after the junction and overlapping of the two or more non-woven fabric layers and of the inner layer of textile polymer net, comprises ultrasound welding of the layers.

GENERAL DESCRIPTION

The present application describes a surgical non-woven fabric swab, with similar visual characteristics to surgical pre-washed gauze swabs, but with a softer and spongy tactile presentation.

Comparing with the majority of articles available on the market, this swab has significant improvements in performance features, including high strength, high capacity and absorption rate and reduced release of fibres and particles.

These aspects are very important points, depending on the intended end use of the article. The use of non-woven fabric in the outer layers is advantageous from the standpoint of article performance, as well as in terms of economic and environmental impact. Both the non-woven fabric as the textile net are made of biocompatible materials and of regular use in other articles in the medical field, therefore not presenting any risk of use.

The surgical swab described in this application is composed of two or more outer layers of non-woven fabric, and an inner layer of textile polymer net, with or without x-ray detectable thread, with high elasticity or high shrinking capacity by application of heat, thereby allowing to obtain a wrinkled or spongy effect in the final article.

After junction and juxtaposition, the layers are joined or welded by ultrasound, forming a laminate. The following is cutting and subsequent contraction/shrinking.

If the textile net comprises elastane, the junction, overlapping and welding are performed under tension, to stay stretched. The cutting causes a stress relaxation, which causes a contraction of the material, originating a very creped structure in the non-woven fabric surfaces, conferring the article an extremely soft and spongy touch.

In case the textile polymer net is comprised by polyamide or polyamide and polyester or even polyamide and cotton, a heat treatment is performed after cutting, which generates a shrinking of the polyamide and, hence, of the surgical swab.

The use of the textile net comprising polyamide does not require an application under tension.

In the product here described, the welding of the layers is carried out by ultrasound and, thus, do not require any addition of binding agent and, hence, needs no drying treatment and no cure of the binding agent.

After the relaxation of the tension or heat treatment, depending on the type of textile net used, a wrinkled and soft effect that is particularly appreciated by users is created. Moreover, these processes are easy to apply and have reduced costs at industrial level. If the products are packed and steam sterilized the heat used in the process also creates the same soft wrinkled surface.

The composition and the surgical swab production process allow working the article in a "flat" presentation until the final stage, when it is then shrinked by heat or relaxation.

This process uses inexpensive materials and constitutes an automatic production process with few steps. Thus, the finished article is produced in a significantly more economical way than with the current productive processes of the surgical gauze swabs. Also inherent to the automation of the production process and total absence of manual intervention is the reduced microbial load that is found in this article, when compared to the surgical gauze swabs, in which production extensive manipulation in folding and sewing exists.

BRIEF DESCRIPTION OF THE FIGURES

For easier understanding of the art, find enclosed the figures that represent preferred embodiments that, however, are not intended to limit the subject matter of this application.

In both situations presented in FIGS. 2 and 3, it is also possible to apply either by welding or by another process a thread or strip, detectable by X-rays (10).

DESCRIPTION OF EMBODIMENTS

Referring to the figures, some embodiments will now be described in more detail, which however are not intended to limit the scope of the present application.

Figure 1:
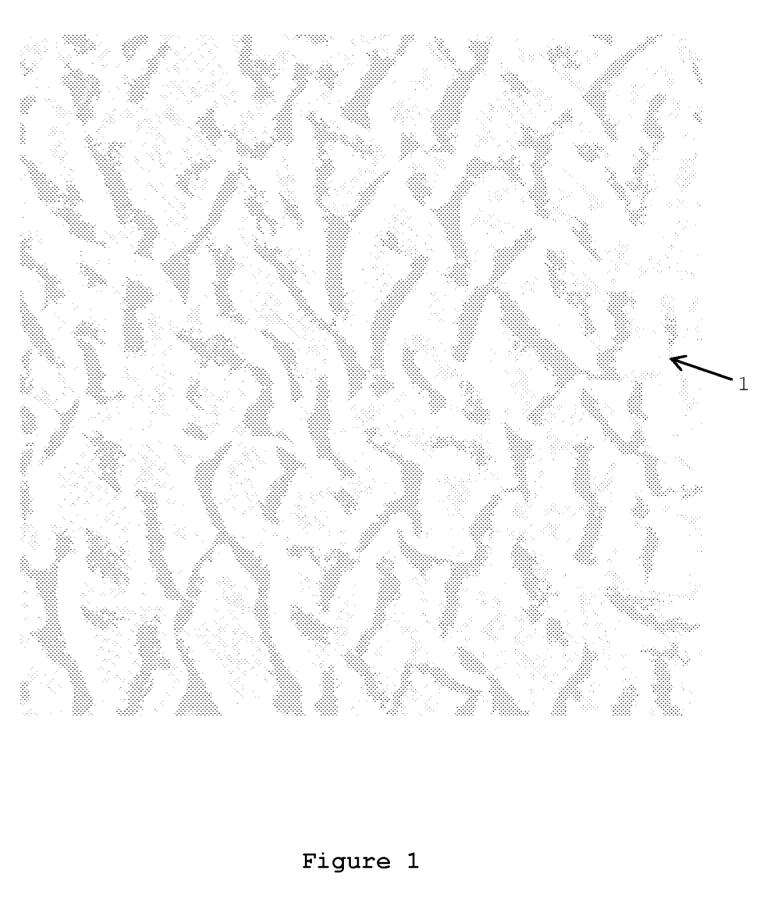
FIG. 1 illustrates a scheme of the surgical non-woven fabric swab with pre-washed aspect (1) in its final presentation.
Figure 2:
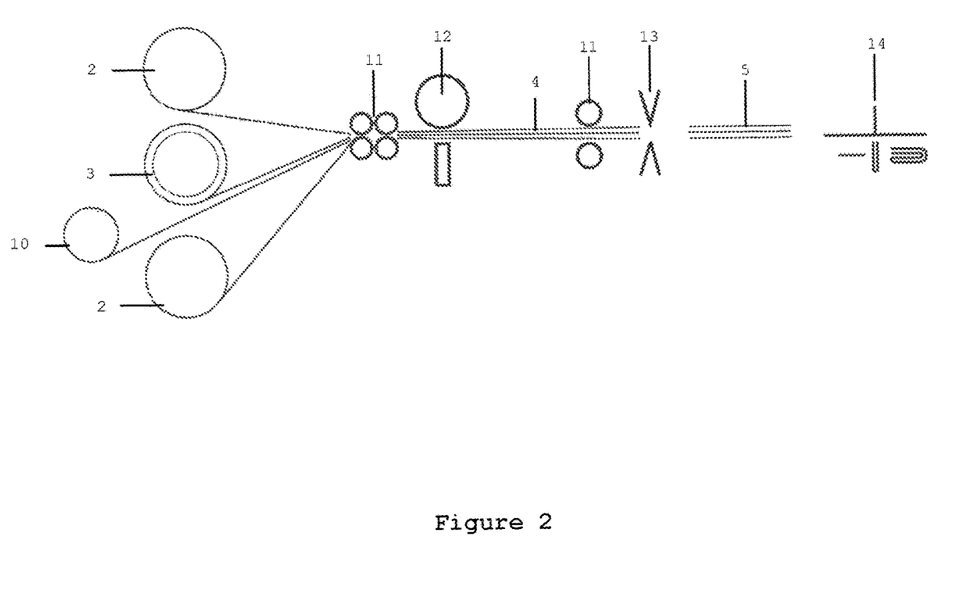
FIG. 2 illustrates, in the case of the textile net comprising a material with high elasticity such as elastane, the swab (1) production process, that passes through the junction of two outer layers of non-woven fabric (2) and an inner layer of elastic textile net, and placed under tension (3) to stay stretched. The three layers are overlapped by pressure rollers (11) and welded together by ultrasound (12), forming the laminate (4) still under tension. Subsequently, the laminate (4) is cut through a blade system (13) to the required dimension. The cutting of the laminate (4) causes relaxation of the textile net, causing it to return to its initial shape, and thus creating a wrinkled effect on the non-woven fabric surfaces to which it has been welded while stretched. Thus, it is obtained the retracted open swab (5) that shifts to an application table of security strips and folds (14) giving rise to the finished article.

In an embodiment and in the case of textile net comprising elastane, the production process of the swab (1) involves the junction of two outer layers of non-woven fabric (2) and an inner layer of elastic textile net, placed under tension (3) to stay stretched. The three layers are overlapped by pressure rollers (11) and welded together by ultrasound (12), forming the laminate (4), still under tension. Subsequently, the laminate (4) is cut to the required dimension through a blade system (13). The cutting of the laminate (4) causes relaxation of the textile net, causing it to return to its initial shape, and thus creating a wrinkled effect on the non-woven fabric surfaces to which it has been welded while stretched. Thus, it is obtained the retracted open swab (5) that shifts to an application table of security strips and folds (14) giving rise to the finished article.

Figure 3:
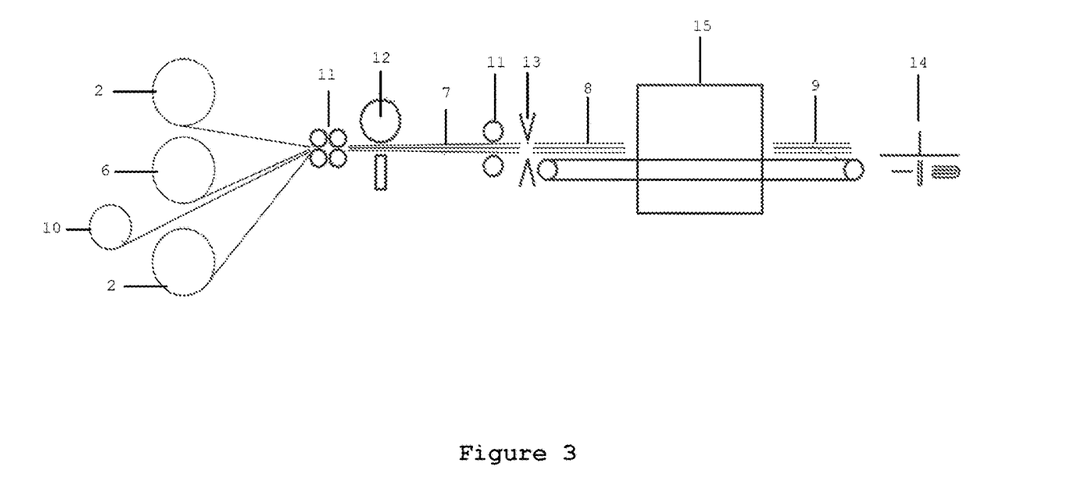
FIG. 3 illustrates a productive scheme for swabs (1) with a textile net comprising polyamide or polyamide and polyester or even polyamide and cotton. The polyamide or polyamide and polyester or cotton textile net (6) is used without applying any tension. The overlapping of non-woven fabric layers (2) and polyamide, polyamide and polyester or polyamide and cotton textile net (6) is carried out by pressure rollers (11). Thereafter the weld is performed by ultrasound (12) giving rise to the laminate (7). The cutting of the laminate into the desired dimension is performed in the blade system (13), thereby obtaining the open swab without shrinking (8). This swab is then subjected to a heat treatment (15) originating the retracted open swab (9). The last step of applying security strips and fold is identical to that described above and performed on the table (14).

In an embodiment and in the case of textile net comprising polyamide or polyamide and polyester or even polyamide and cotton, the production process of the swab involves the junction and overlapping of two outer layers of non-woven fabric (2) and one inner layer of polyamide or polyamide and polyester or even polyamide and cotton textile net, performed by pressure rollers (11). Thereafter, the welding is performed by ultrasound (12) giving rise to the laminate (7). The cutting of the laminate into the desired dimension is performed in the blade system (13), thereby obtaining the open swab without shrinking (8). This swab is then subjected to a heat treatment (15) originating the retracted open swab (9). The last step of applying security strip(s) and fold is identical to that described above and carried out on the table (14).

In a preferred embodiment, the heat treatment is performed at a temperature between 40 and 80° C. At this temperature range also the sterilization by Ethylene Oxide will cause the desired shrinking effect therefore requiring no heat station in the production machine.

In a preferred embodiment, regardless of the type of textile net used, the overlapping of the layers is carried out by pressure rollers.

In a preferred embodiment, regardless the type of textile net used, the cut is made through a blade system.

In one embodiment, applying the security strip is performed so that it becomes fixed at one end. The security strips are kept outside the surgical incision while the swabs are on the inside, to ensure that none swabs is forgotten inside the patient after surgery.

In one embodiment, it is also possible to apply a thread or strip, detectable by X-rays (10). In one embodiment, this application is carried out by welding.

Figure 4:
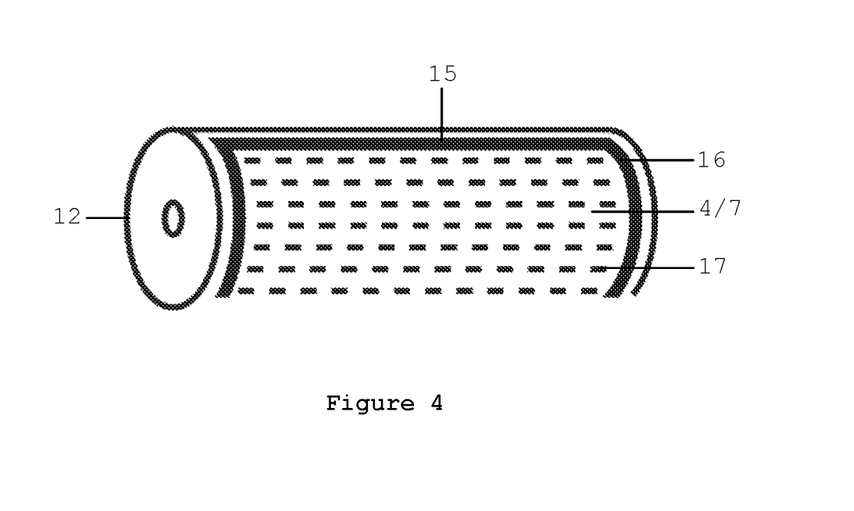
FIG. 4 illustrates the application of ultrasound welding (12) at the ends (15 and 16) and inside (17) the swab simultaneously and through a single roll.
Figure 5:
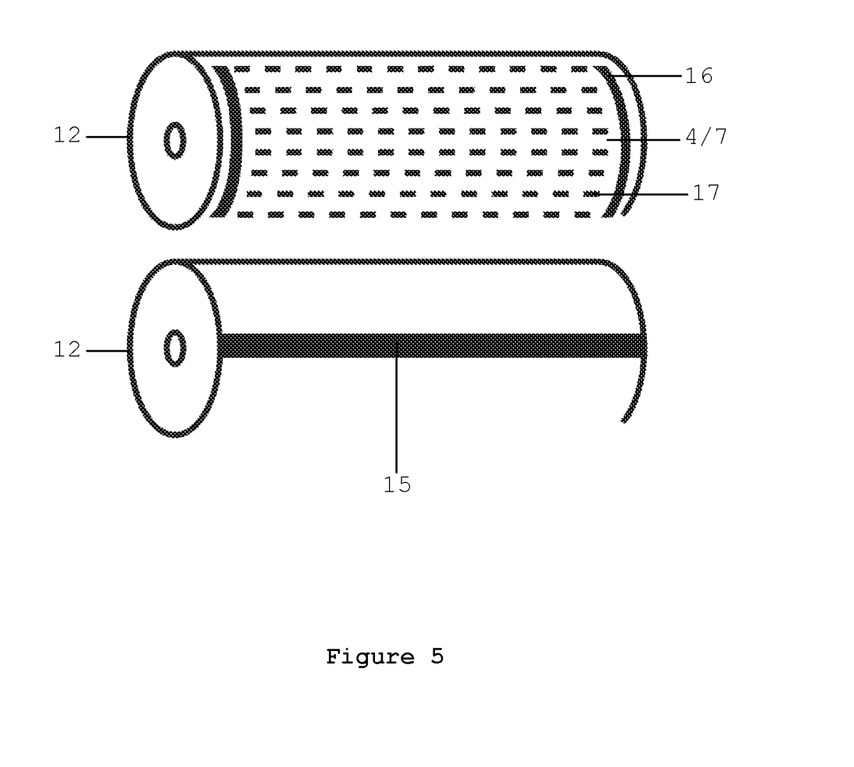
FIG. 5 illustrates the application of ultrasound welding (12) though two different rolls.

As illustrated in FIGS. 4 and 5, there are two alternative methods for the application of ultrasound welding (12) on the non-woven fabric laminate and elastane textiles net (4) or on the laminate with non-woven fabric and polyamide or polyamide and polyester or even polyamide and cotton textile net (7).

In the first roll of FIG. 5, it is performed the outer welding parallel to the roll (16) as well as the internal welding (17), while in the second roll is performed the outer welding perpendicular to the roll (15).

Test Results Carried Out to Swabs

In the following tables are presented the results obtained in the tests carried out to a representative sample of the surgical swab in non-woven fabric, with pre-washed effect, when used in a elastane, polyamide, polyamide and polyester or polyamide and cotton textile net on the inside compared to other options currently available:

Absorption Capacity:

The absorption capacity of the non-woven fabric swab with elastane, polyamide, polyamide and polyester or polyamide and cotton net is considerably higher than the absorption capacity of different types of available swabs.

TABLE 1

Absorption capacity values of the surgical non-woven fabric swab with elastane, polyamide, polyamide and polyester or polyamide and cotton net as compared with other products currently on the market.

| Method | Absorption cap. (%) | Absorption cap. (g/g) | Absorption cap. (g/cm$^2$) |
|---|---|---|---|
| Standard | EN1644-1 | EN1644-2 | 13726-1 |
| Non-woven fabric swab with elastane net | 1048 | 16.5 | 17.7 |
| Non-woven fabric swab with polyamide net | 1236 | 20.6 | 18.7 |
| Non-woven fabric swab with polyamide/polyester net | 1170 | 15.8 | 28.3 |
| Non-woven fabric swab with polyamide/cotton net | 951 | 15.7 | 17.6 |
| Abdominal swab | 966 | 11.3 | 12.0 |
| Non-woven 2 layers | | | |
| Gauze swab 17 threads/cm$^2$ 4 layers | 472 | 6.9 | 7.2 |
| Gauze swab 17 threads/cm$^2$ 4 pre-washed layers | 629 | 9.5 | 14.9 |
| Gauze swab 20 threads/cm$^2$ 4 layers | 447 | 7.5 | 7.9 |
| Gauze swab 20 threads/cm$^2$ 4 pre-washed layers | 640 | 8.8 | 18.3 |

Absorption Rate:

The surgical non-woven fabric swab with elastane, polyamide, polyamide and polyester or polyamide and cotton net presents higher percentage of water retention than the surgical pre-washed gauze swab, after 5 and 10 seconds from the beginning of the test.

Tables 2 and 3—Absorption rate values obtained from a pre-washed gauze surgical swab and for a surgical non-woven fabric swab with elastane, polyamide, polyester and polyamide or polyamide and cotton net at the end of 10 seconds, and 5 seconds, respectively.

TABLE 2

Test time - 10 seconds

| Initial weight (g) swab | Final weight (g) swab + water | Amount of water retained in the swab after 10 seconds (g) | % retained |
|---|---|---|---|
| Pre-washed gauze swab | | | |
| 20.72 | 59.76 | 39.04 | 188 |
| 21.83 | 60.73 | 38.9 | 178 |
| Non-woven fabric swab with elastane net | | | |
| 16.59 | 58.43 | 41.84 | 252 |
| 17.4 | 53.28 | 35.88 | 206 |
| Non-woven fabric swab with polyamide net | | | |
| 16 | 61.93 | 45.93 | 287 |
| 14.6 | 62.95 | 48.35 | 331 |

TABLE 2-continued

Test time - 10 seconds

| Initial weight (g) swab | Final weight (g) swab + water | Amount of water retained in the swab after 10 seconds (g) | % retained |
|---|---|---|---|
| Non-woven fabric swab with polyamide/polyester net | | | |
| 19.54 | 74.48 | 54.94 | 281 |
| 20.06 | 65.21 | 45.15 | 225 |
| Non-woven fabric swab with polyamide/cotton net | | | |
| 14.26 | 44.43 | 30.17 | 212 |
| 14.28 | 43.82 | 29.54 | 207 |

TABLE 3

Test time - 5 seconds

| Initial weight (g) swab | Final weight (g) swab + water | Amount of water retained in the swab after 5 seconds (g) | % retained |
|---|---|---|---|
| Pre-washed gauze swab | | | |
| 20.813 | 57.809 | 37 | 178 |
| 20.714 | 66.21 | 45.5 | 220 |
| 27.81 | 93.62 | 65.81 | 237 |
| 27.082 | 69.41 | 42 | 156 |
| Non-woven fabric swab with elastane net | | | |
| 16.13 | 55.41 | 39.28 | 244 |
| 17.02 | 62.55 | 45.53 | 268 |
| Non-woven fabric swab with polyamide net | | | |
| 14.7 | 71.64 | 56.94 | 387 |
| 14.71 | 66.53 | 51.82 | 352 |
| Non-woven fabric swab with polyamide/polyester net | | | |
| 20.05 | 68.66 | 48.61 | 242 |
| 19.57 | 69.25 | 49.68 | 254 |
| Non-woven fabric swab with polyamide/cotton net | | | |
| 13.91 | 44.5 | 30.59 | 220 |
| 14.27 | 42.85 | 26.58 | 200 |

Release of Fibres and Particles:

The surgical non-woven fabric swab with elastane, polyamide, polyamide and polyester or polyamide and cotton net presents lower amounts of released particles than the surgical pre-washed gauze swab.

TABLE 4

Release values of fibres and particles obtained from a surgical pre-washed gauze swab and for a surgical non-woven fabric swab with elastane, polyamide, polyamide and polyester or polyamide and cotton net.

| ISO 9073-10 | No. Particles ≥0.5 μm |
|---|---|
| Pre-washed gauze swab | approx. 1000000 |
| Non-woven fabric swab with elastane, polyamide, polyamide and polyester or polyamide and cotton net. | <5000 |

Chemical Properties:

The values obtained in the chemical properties tests for the surgical non-woven fabric swab with elastane, polyamide, polyamide and polyester or polyamide and cotton net are within the parameters defined by applicable standards.

TABLE 5

Values obtained for the different chemical properties tests for a surgical pre-washed gauze swab and for a surgical non-woven fabric swab with elastane, polyamide, polyamide and polyester or polyamide and cotton net.

| | Water-soluble substances (%) | Optic White | pH | Substances soluble in nonpolar solvents (%) |
|---|---|---|---|---|
| Pre-washed gauze swab | ≤0.5 | Absent | 6.0-8.0 | ≤0.5 |
| Non-woven fabric swab with elastane net | ≤0.5 | Absent | 6.0-8.0 | ≤0.5 |
| Non-woven fabric swab with polyamide net | ≤0.5 | Absent | 6.0-8.0 | ≤0.5 |
| Non-woven fabric swab with polyamide/polyester net | ≤0.5 | Absent | 6.0-8.0 | ≤0.5 |
| Non-woven fabric swab with polyamide/cotton net | ≤0.5 | Absent | 6.0-8.0 | ≤0.5 |

The present embodiment is not, naturally, in any way restricted to the embodiments described herein and a person of ordinary skills in the area can provide many modification possibilities thereof without departing from the general idea, as defined in the claims.

All embodiments described above are obviously combinable with each other. The following claims further define preferred embodiments.

The invention claimed is:

1. A surgical swab forming a laminate consisting of:
   a first layer of non-metallic and non-woven fabric consisting of a layer of fibers, continuous filaments or chopped threads organized into a net, veil or web by means other than weaving or knitting, wherein loose threads and seams are absent;
   a second layer of non-metallic textile polymer net, optionally having an x-ray detectable thread, the second layer adjacent the first layer, the second layer consisting of a polymer selected from:
   elastane;
   polyamide;
   polyamide and polyester; and
   polyamide and cotton;
   and
   a third layer of non-metallic and non-woven fabric, the third layer adjacent the second layer, the third layer consisting of a layer of fibers, continuous filaments or chopped threads organized into a net by means other than weaving or knitting, wherein loose threads and seams are absent;
   wherein the second layer is disposed between the first layer and the third layer.

2. The surgical swab, according to claim 1, wherein the textile polymer net consists of elastane.

3. The surgical swab, according to claim 1, wherein the textile polymer net consists of polyamide or polyamide and polyester or polyamide and cotton.

4. A production process of the surgical swab described in claim 1, comprising:
   junctioning and overlapping, by pressure rollers, the first layer of non-metallic and non-woven fabric, the second layer of non-metallic textile polymer net adjacent the first layer, and the third layer of non-metallic and non-woven fabric adjacent the second layer;

ultrasound welding the first, second, and third layers to form a laminate; and cutting the laminate.

5. The production process, according to claim 4, wherein the textile polymer net is elastane.

6. The production process, according to claim 4, wherein the textile polymer net is polyamide, or polyamide and polyester or polyamide and cotton.

7. The production process according to claim 4, wherein the textile polymer net is obtained through weaving or knitting.

8. The production process according to claim 5, wherein the junctioning, overlapping and welding steps are carried out under tension.

9. The production process according to claim 6, further comprising applying a heat treatment, after cutting, at a temperature between 40 and 80° C., to generate a shrink-wrapping of the surgical swab.

10. The production process according to claim 4, wherein the cutting is carried out through a blade system.

11. The production process according to claim 4, further comprising applying a security strip.

12. The production process according to claim 4, further comprising a folding step of the surgical swab.

13. The production process according to claim 4, further comprising applying a thread or strip detectable by X-rays.

* * * * *